(12) United States Patent
Cleary

(10) Patent No.: US 6,988,888 B2
(45) Date of Patent: Jan. 24, 2006

(54) MANDIBULAR REPOSITIONING ASSEMBLY

(75) Inventor: James D. Cleary, Glendora, CA (US)

(73) Assignee: 3M Innovative Properties Company, St. Paul, MN (US)

(*) Notice: Subject to any disclaimer, the term of this patent is extended or adjusted under 35 U.S.C. 154(b) by 9 days.

(21) Appl. No.: 10/427,161

(22) Filed: Apr. 30, 2003

(65) Prior Publication Data

US 2004/0219474 A1 Nov. 4, 2004

(51) Int. Cl.
*A61C 7/00* (2006.01)
(52) U.S. Cl. .................................... 433/19
(58) Field of Classification Search ............ 433/19, 433/18, 7, 20, 21, 22
See application file for complete search history.

(56) References Cited

U.S. PATENT DOCUMENTS

| | | | |
|---|---|---|---|
| 934,958 A | 9/1909 | Case | |
| 3,315,359 A | 4/1967 | Moss | |
| 3,798,773 A | 3/1974 | Northcutt | |
| 3,997,970 A | 12/1976 | Hodgson | |
| 4,382,783 A | 5/1983 | Rosenberg | |
| 4,462,800 A | 7/1984 | Jones | |
| 4,525,143 A | 6/1985 | Adams | |
| 4,551,095 A | 11/1985 | Mason | |
| 4,618,324 A | 10/1986 | Nord | |
| 4,708,646 A | 11/1987 | Jasper | |
| 4,795,342 A | 1/1989 | Jones | |
| 5,074,784 A * | 12/1991 | Sterrett et al. | 433/18 |
| 5,183,388 A | 2/1993 | Kumar | |
| 5,352,116 A | 10/1994 | West | |
| 5,435,721 A | 7/1995 | Vogt | |
| 5,562,445 A | 10/1996 | DeVincenzo et al. | |
| 5,645,423 A | 7/1997 | Collins, Jr. | |
| 5,645,424 A | 7/1997 | Collins, Jr. | |
| 5,651,672 A | 7/1997 | Cleary et al. | |
| 5,678,990 A | 10/1997 | Rosenberg | |
| 5,711,667 A | 1/1998 | Vogt | |
| 5,718,576 A | 2/1998 | Schnaitter et al. | |
| 5,738,514 A | 4/1998 | DeVincenzo et al. | |
| 5,829,975 A | 11/1998 | Gold | |
| 5,944,518 A * | 8/1999 | Sabbagh | 433/19 |
| 5,964,588 A | 10/1999 | Cleary | |
| 5,980,247 A | 11/1999 | Cleary | |
| 6,113,390 A * | 9/2000 | Sirney et al. | 433/19 |
| 6,120,289 A | 9/2000 | Cleary et al. | |

(Continued)

FOREIGN PATENT DOCUMENTS

| | | |
|---|---|---|
| DE | 195 26 474 | 1/1997 |
| FR | 2 087 079 | 12/1971 |
| FR | 2 702 141 | 9/1994 |
| FR | 2813783 A1 * | 3/2002 |

OTHER PUBLICATIONS

Eureka Springl, Clinical Information, 1996.

(Continued)

*Primary Examiner*—Melba N. Bumgarner
(74) *Attorney, Agent, or Firm*—James D. Christoff

(57) ABSTRACT

A device for correcting the relative position of the jaws of an orthodontic patient includes a telescoping assembly along with a coil spring. As the patient's jaws are closed, the telescoping assembly exerts a force against the spring which tends to posture the jaws in correct occlusal relationship. The coil spring provides a yieldable force that avoids the need for a rigid, hard stop as the patient's jaws are closed.

21 Claims, 3 Drawing Sheets

U.S. PATENT DOCUMENTS

| | | | |
|---|---|---|---|
| 6,168,430 B1 * | 1/2001 | Higgins | 433/19 |
| 6,302,688 B1 | 10/2001 | Jordan et al. | |
| 6,361,315 B1 | 3/2002 | Hanks | |
| 6,547,560 B1 | 4/2003 | Vazquez | |
| 6,669,474 B2 * | 12/2003 | Vogt | 433/19 |

OTHER PUBLICATIONS

"The Swedish-Style Integrated herbst Appliance", Haegglund and Segerdal, The Journal of Clinical Orthodontics, Jun. 1997, pp. 378-390.

U.S. Appl. No. 09/848,030, filed May 3, 2001.

* cited by examiner

MANDIBULAR REPOSITIONING ASSEMBLY

BACKGROUND OF THE INVENTION

1. Field of the Invention

This invention relates to a device useful during orthodontic treatment for repositioning the mandibular jaw. More specifically, this invention relates to a mandibular repositioning device for urging the lower jaw in a forward direction relative to the upper jaw in order to improve occlusion.

2. Description of the Related Art

Orthodontic treatment involves movement of malpositioned teeth to orthodontically correct positions. During treatment, tiny orthodontic appliances known as brackets are often connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to the patient's molar teeth. The brackets, archwires and buccal tubes are commonly referred to as "braces".

The orthodontic treatment of some patients include correction of the alignment of the upper dental arch with the lower dental arch. For example, certain patients have a condition referred to as a Class II malocclusion where the lower dental arch is located an excessive distance in a rearward direction relative to the location of the upper dental arch when the jaws are closed. Other patients may have an opposite condition referred to as a Class III malocclusion wherein the lower dental arch is located in a forward direction of its desired location relative to the position of the upper dental arch when the jaws are closed.

Orthodontic treatment of Class II malocclusions are commonly corrected by movement of the upper dental arch as a single unit relative to movement of the lower dental arch as a single unit. To this end, forces are often applied to each dental arch as a unit by applying force to the brackets or buccal tubes, the archwires, or attachments connected to the brackets, buccal tubes, or archwires. In this manner, a Class II malocclusion can be corrected at the same time that the archwires and the brackets are used to move individual teeth to desired positions relative to each other.

Correction of Class II malocclusions is sometimes carried out by use of a force-applying system known as headgear that includes strapping which extends around the rear of the patient's head. The strapping is often connected by tension springs that, in turn, are connected to the buccal tubes, the brackets or one of the archwires.

However, headgear is often considered unsatisfactory because it is visibly apparent. Headgear may serve as a source of embarrassment, particularly among child and teenage patients who may experience teasing from classmates. The embarrassment can be somewhat reduced if the orthodontist instructs the patient to wear the headgear only at night, but unfortunately such practice may lengthen treatment time since the desired corrective forces are applied during only a portion of each calendar day.

Consequently, many practitioners and patients favor the use of intra-oral devices for correcting Class II malocclusions. Such devices are often located near the cuspid, bicuspid and molar teeth and away from the patient's anterior teeth. As a result, intra-oral devices for correcting Class II malocclusions are hidden in substantial part once installed and eliminate much of the patient embarrassment that is often associated with headgear.

Orthodontic force modules made of an elastomeric material have been used in the past to treat Class II malocclusions by connecting a pair of such force modules between the dental arches on opposite sides of the oral cavity. Elastomeric force modules are often used in tension to pull the jaws together in a direction along references lines that extend between the points of attachment of each force module. Such force modules may be an O-ring or a chain-type module made of a number of integrally connected O-rings. However, these modules are typically removable by the patient for replacement when necessary, since the module may break or the elastomeric material may degrade during use to such an extent that the amount of tension exerted is not sufficient.

Unfortunately, orthodontic devices such as headgear and removable force modules are not entirely satisfactory for use with some patients, because the effectiveness of the devices is dependent upon the patient's cooperation. Neglect of the patient to faithfully wear the headgear each day or install new elastomeric force modules as appropriate can seriously retard the progress of treatment and defeat timely achievement of the goals of an otherwise well-planned treatment program, resulting in an additional expenditure of time for both the patient and the orthodontist.

As a result, a number of intra-oral devices that are non-removable by the patient have been proposed in the past to overcome the problems of patient cooperation associated with headgear and with removable intra-oral force modules. For example, U.S. Pat. Nos. 3,798,773, 4,462,800 and 4,551,095 disclose telescoping tube assemblies that urge the jaws toward positions of improved alignment. The assemblies are securely coupled to other orthodontic appliances such as brackets or buccal tubes by the practitioner, and the problems of patient non-compliance are avoided.

An improved telescoping, intra-oral force module is described in applicant's U.S. Pat. No. 5,964,588. This module includes a first tubular member, a second tubular member slidably received in the first member and a third member that is slidably received in the second member. A helical spring extends around the second member for urging the second member and the first member in directions away from each other. The three members allow the jaws to be opened widely without separation of one member relative to the other two members.

Other orthodontic devices for correcting Class II malocclusions are described in U.S. Pat. Nos. 4,708,646, 5,352, 116, 5,435,721 and 5,651,672. The devices described in these references include flexible members that are connected to upper and lower jaws of a patient. The length of the members is selected such that the member is curved in an arc when the patient's jaws are closed. The members have an inherent bias that tends to urge the members toward a normally straight orientation to provide a force that pushes one jaw forwardly or rearwardly relative to the other jaw when the jaws are closed.

U.S. Pat. Nos. 5,645,424 and 5,678,990 describe intra-oral devices for correcting Class II malocclusions having linkage that includes pivotal connections. The devices in both of these references have a somewhat overall "Z"-shaped configuration. A device having a somewhat similar overall configuration is shown in U.S. Pat. No. 5,645,423 and includes double helical loops located on each side of a central segment. A device having a different configuration is set out in applicant's U.S. Pat. No. 5,980,247.

The intra-oral devices described in the aforementioned U.S. Pat. Nos. 5,645,423, 5,645,424 and 5,678,990 have outer arms or shanks for connection to respective tubes. One of the tubes is connected to a molar tooth of the patient's upper dental arch and the other tube is coupled to a molar tooth of the patient's lower dental arch. It is an advantage to connect such intra-oral devices to the molar teeth of both arches, because the relatively large size of the roots of the molar teeth provides a good anchoring location for applying forces to move one jaw relative to the other jaw.

Some practitioners have a preference to use a device that applies a spring force to one or both dental arches when the patient's jaws are closed. These devices are often constructed so that the patient does not experience a "hard stop" as the teeth come together. However, the biasing force provided by the spring tends to move the dental arches relative to each other over a period of time.

Other practitioners prefer to use a device that reaches a hard, fixed limit as the jaws are closed. An example of such a device is the Herbst appliance, which includes a telescoping tube assembly. It is sometimes believed that these devices are more effective in moving the arches relative to each other for a given length of treatment time, since the jaws must reposition themselves each time the jaws are closed. These devices are considered especially effective when the patient is relatively young and bone growth is still proceeding at a relatively fast rate.

However, some of the devices known in the past for repositioning the dental arches are considered to present problems when a hard stop is provided as the jaws are closed. Specifically, if the jaws tend to posture to a Class II relationship during jaw closure, the resulting forces on various appliances in the oral cavity can be significant. The strength of the muscles of mastication, and particularly the masseter muscle, can produce significant force as the jaws are closed. This force may fracture the device or other components connected to the device, or cause attachments such as brackets and buccal tubes to be detached from the teeth.

Fracture or detachment of the jaw repositioning devices or accompanying components during the course of treatment is a nuisance to both the practitioner and the patient. When breakage occurs, the patient should return immediately to the orthodontist for replacement of the broken components so that treatment can resume. There is also the possibility that the broken components may contact and injure the oral tissue and cause significant pain.

In the past, a common response to the problem of breakage as mentioned above has been to provide stronger components, such as larger and stiffer assemblies. In addition, crowns are sometimes placed over the molar teeth and used as attachments rather than buccal tubes so that the risk of detachment from the tooth is reduced. However, such modifications are not considered entirely satisfactory due to the increased bulk and expense of the replacement components.

In an article entitled "*The Swedish-Style Integrated Herbst Appliance*" by Drs. Paul Haegglund and Staffan Segerdal, The Journal of Clinical Orthodontics, June 1997, pages 378–390, the authors describe the use of a Herbst appliance that is connected on its lower end to an auxiliary archwire. The auxiliary archwire extends in parallel relationship to the lower archwire and is slidably received in auxiliary passages of lower buccal tubes mounted on each side of the mandibular arch. An anterior section of the auxiliary archwire is coupled by elastomeric modules to the lower, main archwire or to hooks connected to the lower archwire.

The elastomeric modules described in the preceding article served as a force limiting device that tended to reduce the probability of appliance breakage or detachment. However, the resistance to tensile forces of elastomeric modules may deteriorate over a period of time. In addition, the force limiting or shock-absorbing effect provided by the elastomeric modules is dependent on the freedom of the auxiliary archwire to slide in the auxiliary passages of the buccal tubes, and such sliding freedom may be hindered by the difficulty of sliding a curved section of the auxiliary archwire within a buccal tube passage that has a straight configuration.

As can be appreciated, there is a need in the orthodontic art for a new device that is effective in repositioning the jaws of patient with a Class II malocclusion. A device is needed that functions reliably and efficiently, and yet is not prone to breakage or likely to cause adjacent components such as buccal tubes to be detached from the associated teeth.

SUMMARY OF THE INVENTION

The present invention is directed to an orthodontic device that connects the upper and lower jaws, and urges the lower jaw to posture toward a position of proper occlusion or Class I relationship when the jaws are closed. The device includes a telescoping assembly having a force limiting spring at one end, and the spring has a central axis that extends in a direction generally along the dental arch. The spring is connected to a molar appliance and serves as a force limiting means. The device functions reliably and effectively for the duration of treatment, and the spring reduces the possibility that the device or other components will fracture or detach from the patient's teeth.

In more detail, the present invention in one aspect is related to a mandibular repositioning device for an orthodontic patient that comprises a first tubular member and a second member slidably received in the first member. The second member has an outer end portion. The first member and the second member extend between the upper and lower jaw of the patient. A coil spring is connected to the outer end portion and has a central axis that extends in a direction generally parallel to the occlusal plane of the patient.

Another aspect of the present invention is directed to an orthodontic brace for moving the relative positions of the mandibular and maxillary dental arches. The brace in this aspect includes an orthodontic attachment for connection to a tooth, and a telescoping assembly having a first member and a second member slidably received in the first member. The second member has an outer end portion. The brace also includes a coil spring that is connected to the outer end portion and to the orthodontic attachment. The coil spring has a central axis that extends generally along a path parallel to the occlusal plane.

An additional aspect of the present invention is also directed toward an orthodontic brace for moving the relative positions of the mandibular and maxillary dental arches. The brace comprises an orthodontic attachment for connection to a tooth, and a wire segment coupled to the attachment and extending along one of the dental arches. The brace further includes a telescoping assembly having a first member and a second member slidably received in the first member. The second member has an outer end portion. The brace also includes a coil spring that is connected to the outer end portion. The wire segment extends through the coil spring in coaxial relation.

In certain embodiments of the invention, an adjustable coupling interconnects the coil spring and the attachment. The coupling enables the correction force applied by the brace to be applied in stages, thereby reducing the possibility of imposing trauma to the patient.

Preferably, the telescoping assembly includes a third member that is slidable relative to the first member. The provision of three members helps to reduce the probability that the members might detaching from one another as the jaws are fully opened.

These and other aspects of the invention are described in more detail in the text that follows and are illustrated in the accompanying drawings.

DETAILED DESCRIPTION OF THE PREFERRED EMBODIMENTS

Figure 1:
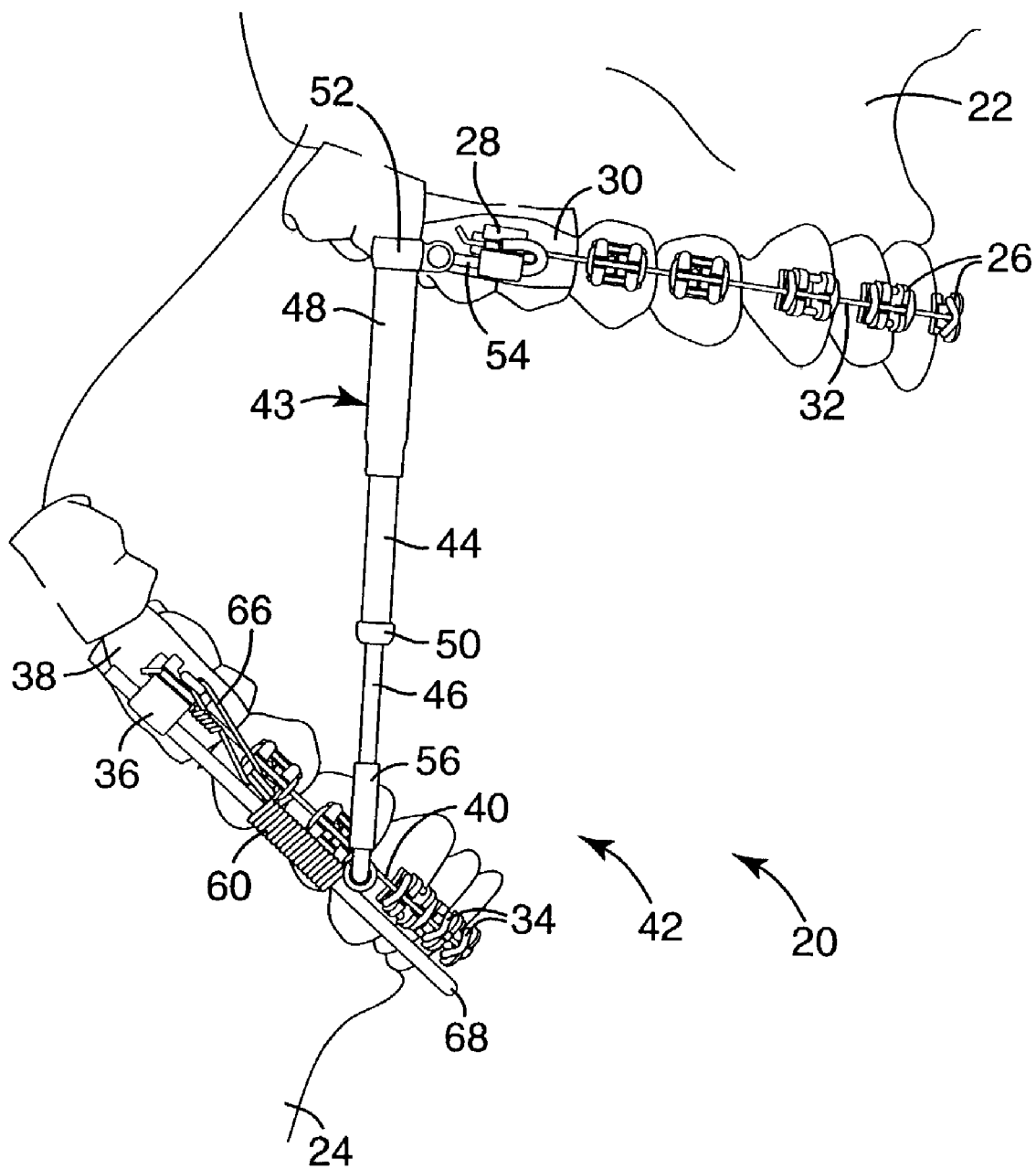
FIG. 1 is a schematic side view of an upper and lower dental arch of a patient undergoing orthodontic treatment, wherein a mandibular repositioning device according to one embodiment of the present invention is illustrated.

FIG. 1 is an exemplary illustration of a patient undergoing orthodontic treatment. An orthodontic brace, generally designated by the numeral 20, is connected to the upper or maxillary jaw 22 of the patient as well as to the lower or mandibular jaw 24 of the patient. The jaws 22, 24 are shown in their fully open position in FIG. 1.

The brace 20 includes a series of upper appliances or brackets 26 that are connected to anterior, cuspid and bicuspid teeth of the upper jaw 22. The brace 20 also includes a molar appliance such as a buccal tube 28 that is connected to the upper right first molar tooth. In this example, the buccal tube 28 is fixed to an orthodontic band 30 that encircles the first molar tooth. An upper archwire 32 extends through slots of the upper brackets 26 as well as through a passage in the buccal tube 28.

The brace 20 further includes a series of lower appliances or brackets 34 that are fixedly connected to the anterior, cuspid and bicuspid teeth of the lower jaw 24. A molar appliance such as a buccal tube 36 is mounted on a band 38 that, in turn, encircles the patient's lower right first molar tooth. A lower archwire 40 extends through slots of the lower brackets 34 as well as through a passage in the lower buccal tube 36.

The brackets 26, 34 illustrated in FIG. 1 are stainless steel brackets that are directly bonded to the enamel surfaces of the teeth. However, a variety of other types of brackets may also be employed. For example, brackets made of translucent alumina or plastic may be used. Brackets that are welded to bands may also be used. As an additional option, the buccal tubes 28, 36 may be directly bonded to the molar teeth so long as the bond has sufficient strength to resist fracture during the course of treatment.

The brackets 26, 34 that are depicted in FIG. 1 are each used in conjunction with an elastomeric O-ring that serves to ligate the corresponding archwire 32, 40 to the bracket body. However, as an alternative, self-ligating brackets may be used. Examples of preferred self-ligating brackets are described in U.S. Pat. No. 09/848,030 filed May 3, 2001.

The brace 20 also includes a mandibular repositioning device 42 that interconnects the upper jaw 22 and the lower jaw 24. The repositioning device 42 is shown in more detail in FIGS. 2 and 3, and is shown alone in FIG. 3. The device 42 includes a telescoping assembly 43 that includes at least two members and preferably includes three members. In the illustrated embodiment, the device 42 includes a first member 44, a second member 46 and a third member 48.

The first member 44 is tubular and has a lower end that is capped with a stop 50 having a central opening. The opposite end of the first member 44 is radially enlarged in stepped fashion. An upper end portion of the first member 44 is slidably received in the third member 48. A lower end portion of the third member 48 is radially narrowed and presents an inner diameter that is less than the outer diameter of the enlarged upper end of the first member 44. The enlarged upper end of the first member 44 cannot slide past the lower, narrowed end portion of the third member 48 and as a result a limit to outward travel is provided.

An upper end portion of the third member 48 includes a connector 52 having a hole. As illustrated in FIG. 1, a pin 54 couples the connector 52 to an orthodontic appliance such as the upper buccal tube 28. However, other types of couplers, such as links or wire loops, may be used in place of the pin 54.

The pin 54 includes a shank that extends through the hole of the connector 52, and an enlarged head of the pin 54 retains the connector 52 on the pin shank. The shank is also bent to a generally "L"-shaped configuration and has a size that is adapted to fit within the passage of the buccal tube 28. Once the pin shank is inserted in the passage, an outer end section of the shank is bent in an arc as depicted in FIG. 1 in order to securely connect in linked fashion the third member 48 to the buccal tube 28 and the associated molar tooth.

Figure 3:
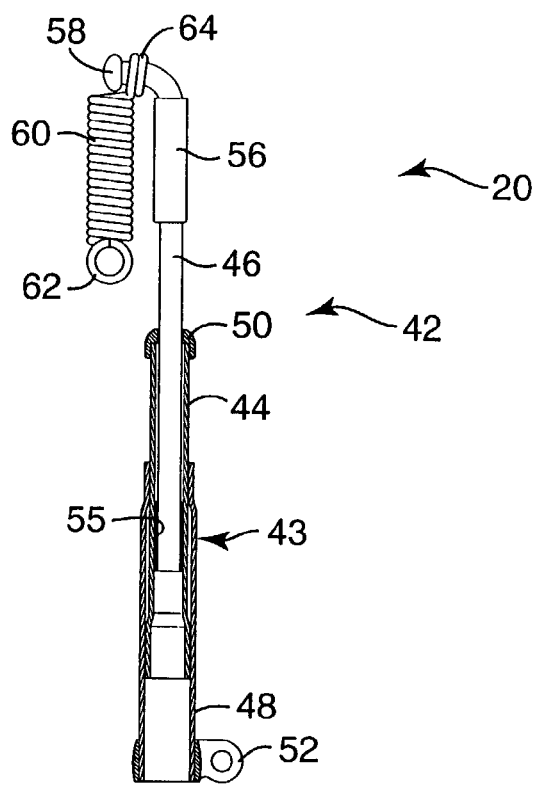
FIG. 3 is an enlarged side view in partial cross-section of the device alone that is depicted in FIGS. 1 and 2.

An upper portion of the second member 46 is slidably received in the lower portion of the tubular first member 44 and includes a cylindrical sleeve 55 (FIG. 3). The outer diameter of the sleeve 55 is larger than the central opening of the stop 50. The sleeve 55 limits the extent of outward (downward) movement of the second member 46 within the first member 44, and retains the members 44, 46 in assembled relationship.

Figure 2:
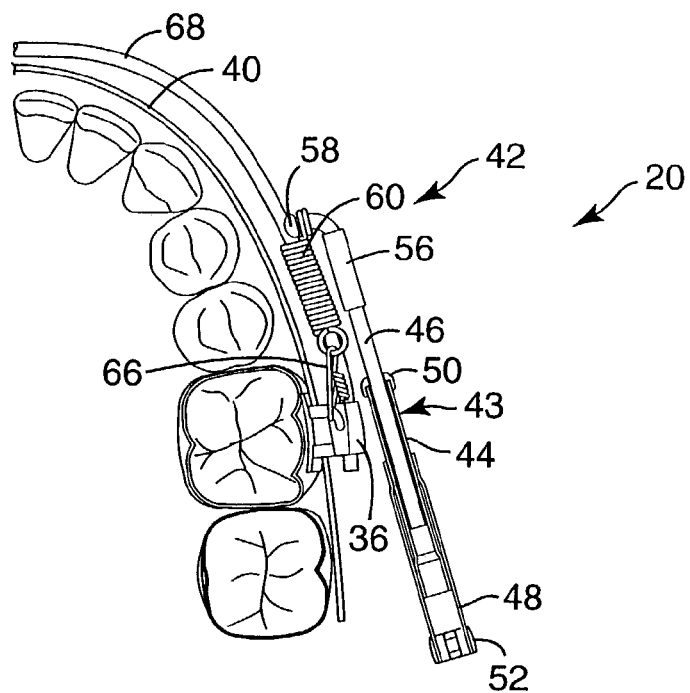
FIG. 2 is a partial, schematic plan view of the lower dental arch and repositioning device shown in FIG. 1, except that the brackets depicted in FIG. 1 are omitted for purposes of clarity, and wherein the repositioning device is shown in partial cross-sectional view.

The second member 46 includes a collar 56 having an outer diameter that is larger than the opening of the stop 50. The collar 56 serves to limit upward movement of the second member 46 into the first member 44 as will be described in more detail below. In this embodiment, the second member 46 has a solid, circular cross-sectional configuration, although other configurations are also possible A lower section of the second member 46 is bent in an arc as shown in FIGS. 2 and 3 and presents an enlarged head 58. A coil tension member or spring 60 is connected to the lower section of the second member 46. The helical spring 60 includes a mesial end segment with a mesial loop 64 (FIG. 3) that extends about the second member 46 adjacent the head 58. The opening of the loop 64 is smaller than the outer diameter of the head 58 as well as the outer diameter of the adjacent collar 56, such that the loop 64 is retained in place between the same.

The spring 60 also includes a distal end segment with a distal loop 62 (FIG. 3) that is remote from the mesial loop 64. As illustrated in FIGS. 1 and 2, the distal loop 62 is coupled to the lower buccal tube 36 by a wire section 66. The wire section 66 has an initially straight configuration or alternatively has an initially generally "U"-shaped configuration, and is formed into a loop by the practitioner. Outer ends of the wire section 66 are twisted together by the practitioner with a hand instrument to retain the wire section 66 in the shape of a closed loop.

The wire section 66 provides a link or coupling between the spring 60 and the lower buccal tube 36. However, other types of couplings are also possible. For example, a pin, somewhat similar to pin 54, may be instead provided. Moreover, the wire section 66 in the illustrated embodiment extends about a hook of the buccal tube 36, although as an alternative it is possible for the wire section 66 to extend through a passage of the buccal tube 36 or connect to other appliances, preferably molar appliances.

An elongated wire segment 68 extends along the lower dental arch as well as through the center of the spring 60 in coaxial relationship. A distal end portion of the wire segment 68 extends through a passage in the lower buccal tube 36. Optionally, the outer, distal end of the wire segment 66 that extends past the buccal tube 36 in a distal direction is provided with a stop or is bent at an angle to ensure that the wire segment 66 does not inadvertently detach from the buccal tube 36. Preferably, the wire segment 68 is relatively stiff and does not deflect significantly in a downward direction as the patient's jaws 22, 24 are closed.

Preferably, the wire segment 68 is a labial bow that extends along the major extent of the lower dental arch. For example, the wire segment 68 extends from the buccal tube 36 that is secured to the lower right first molar tooth to the buccal tube (not shown) that is secured to the lower left first molar tooth. Preferably, the wire segment 68 extends in a curved path that is substantially parallel to the path of the lower archwire 40. Optionally, although not necessarily, a wire loop or elastomeric module (not shown) may be connected between the wire segment 68 and the lower archwire 40 in a location adjacent the lower anterior teeth in order to help retain the wire segment 68 in a plane parallel to the plane of the lower archwire 40 as the jaws 22, 24 are closed and resist downward deflection.

Although not depicted in the drawings, it should be understood in this regard that the opposite side of the oral cavity preferably includes orthodontic components similar to the components depicted in FIGS. 1–3 and mounted in mirror-image fashion. Specifically, the patient's upper and lower left first molar teeth are attached to buccal tubes similar to the tubes 28, 36 respectively, and a repositioning device similar to the repositioning device 42 is provided on the left side of the patient's oral cavity in a manner similar to the placement and connection of the repositioning device 42 illustrated in FIG. 1. As a consequence, the resultant corrective force presented by the two repositioning devices for repositioning the jaws is substantially balanced on both sides of the oral cavity.

Advantageously, the provision of the three members 44, 46, 48 helps to ensure that the assembly 43 does not come apart when the patient's jaws are in a fully open position. Such construction is an advantage over two-member telescoping assemblies as known in the past. The enlarged upper end portion of the first member 44, in combination with the restricted lower end opening of the third member 48, serves to retain the members 44, 48 in assembled relationship. The sleeve 55, in combination with the restricted central opening of the stop 50, serves to retain the members 44, 46 in assembled relationship. Optionally, the length of the second member 46 and of the collar 56 may vary, so that the practitioner can select the best length for the patient at hand.

Figure 4:
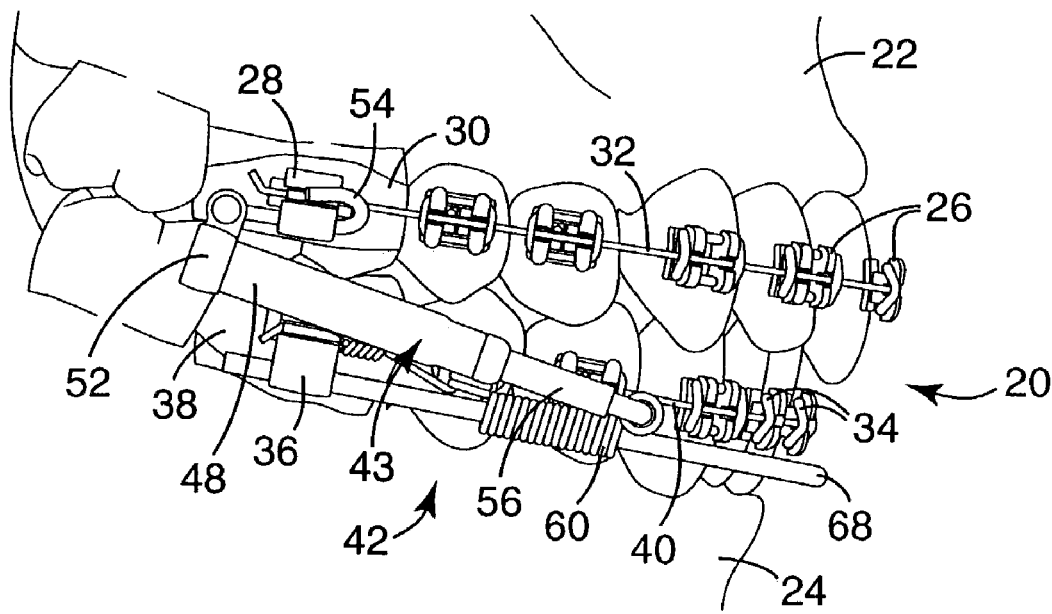
FIG. 4 is a view somewhat similar to FIG. 1 except that the patient's jaws are closed, wherein the lower jaw is illustrated in Class I relationship relative to the upper jaw.

FIG. 4 is an illustration of the patient's oral cavity when the jaws 22, 24 are closed and postured in a Class I relationship. In this position of the jaws 22, 24, relatively little force is exerted on the repositioning device 42 and the coil spring 60 is not extended to any appreciable extent. To this end, the length of the looped wire section 66 is selected and adjusted as needed by the practitioner so that little, if any, extension of the spring 60 occurs when the jaws 22, 24 are in proper Class I relationship.

Figure 5:
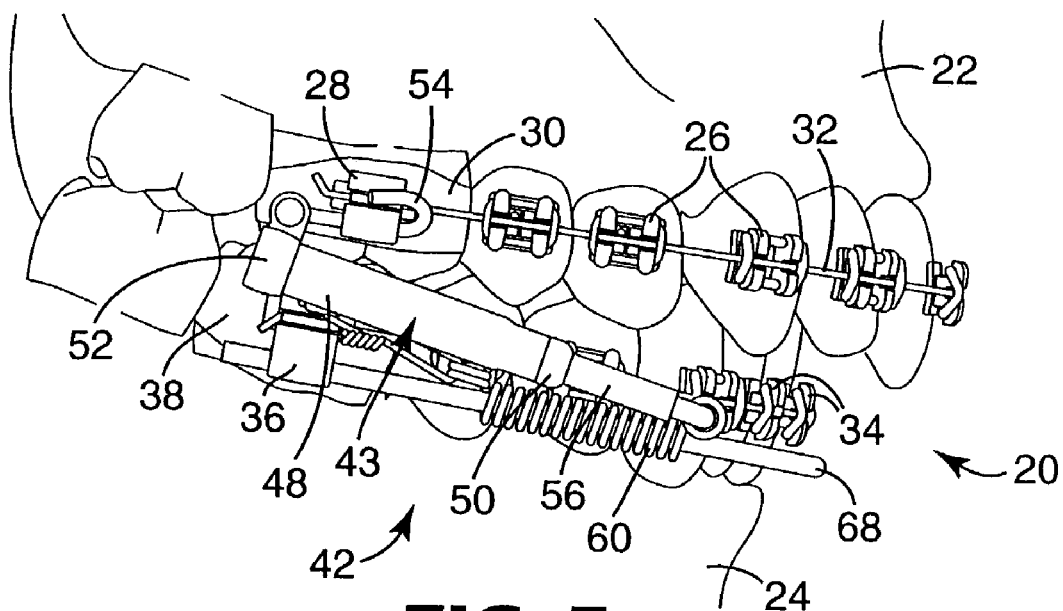
FIG. 5 is a view somewhat similar to FIG. 4 except that the lower jaw is illustrated in a Class II relationship relative to the upper jaw, such that a biasing force presented by a spring of the device functions to urge the lower jaw forwardly relative to the upper jaw.

FIG. 5 is an illustration that also shows the jaws 22, 24 closed, but in this instance the lower jaw 24 has postured back to a Class II relationship relative to the upper jaw 22. As depicted, the telescoping members 44, 46, 48 are now fully compressed such that the stop 50 bears against the lower end of the third member 48 and the collar 56 bears against the stop 50. In addition, the coil spring 60 is extended. The biasing tension force presented by the spring 60 urges the lower buccal tube 36 in a direction toward the lower end of the second member 46, with the result that the lower jaw 24 tends to shift in a forward direction relative to the upper jaw 22.

The spring constant of the spring 60 is selected so that the spring is begins to extend whenever the force exerted by the telescoping assembly 43 in a generally mesial direction exceeds a certain amount. An example of a suitable spring is a spring that begins to extend whenever the tensile forces exerted on the spring exceed approximately 0.5 lbs (0.2 kg) and, when extended by 0.1 inch (2.5 mm), exerts a tensile force of approximately 2 lbs (0.9 kg). However, springs that are stronger or weaker may also be employed in accordance with the particular treatment program and/or the particular orthodontic appliances and other components selected by the practitioner.

The relationship of the spring 60 and the wire segment 68 provides an important advantage, in that the wire segment 68 stabilizes the position of the spring 60 so that its resultant force is directed in a proper orientation. In practice, the wire segment 68 is preferably relatively stiff and does not deflect downwardly to any appreciable extent as the patient's jaws 22, 24 are closed. As a consequence, the spring 60 tends to expand and contract along a path that is parallel to the occlusal plane, and the direction of the resultant repositioning force is predictably maintained. As can be understood by viewing FIGS. 1, 4 and 5, as the jaws 22, 24 close, the members 44, 46, 48 of the telescoping assembly 43 move along a reference axis that extends at a non-zero angle relative to the central axis of the spring 60 and the direction of extension of the wire segment 68.

In embodiments where the wire segment 68 extends from a lower left molar tooth to a lower right molar tooth, the wire segment 68 helps to prevent undue tipping of the molar teeth as the repositioning force is applied to the jaws 22, 24. Specifically, the wire segment 68 reduces the likelihood that the long axis of the molar teeth will pivot in an arc wherein the crowns of the teeth tip in a mesial direction. Such construction helps to avoid the need for correcting the orientation of the molar teeth during a subsequent phase of treatment.

Importantly, the repositioning device 42 does not provide a hard, solid stop when the jaws 22, 24 are closed. Instead, the spring 60 provides a gradual increase in tension force as the jaws 22, 24 close. Such construction helps to ensure that the forces imposed on various components of the brace 20 are not excessive and do not cause fatigue or fracture. In addition, such construction helps ensure that the various tooth attachments, including the brackets and the buccal tubes, remain firmly connected to the teeth.

Over a period of time, the repositioning device 42 shifts the jaws 22, 24 toward a permanent Class I relationship. As the position of the jaws is corrected, the spring 60 is not extended as far during jaw closure and consequently provides less force in tension. In response, the practitioner may elect to progressively reactivate the repositioning device 42 by reducing the length of the looped wire section 66. Such practice shifts the distal loop 62 toward a position closer to the lower buccal tube 36 and thus the position of the distal end segment or distal loop 62 relative to the buccal tube 36 is incrementally adjusted. As a result, the spring 60 thereafter is extended an increased distance when the jaws 22, 24 are postured in a Class II relationship and provides additional force in tension.

Other embodiments of the invention are also possible. For example, the spring 60 may be a compression spring and located on the mesial side of the head 58. Optionally, the compression spring may extend along the anterior extent of the wire segment 68, from the second member 46 of one repositioning device 42 to the second member of the other. However, the construction illustrated in the drawings is preferred since a solid, hard stop is more likely to be avoided.

The description set out above is intended to provide an understanding of the beneficial features and aspects of the present invention. However, those skilled in the art will recognize that other embodiments, including additions and substitutions of various components, are possible without departing from the essence of the invention. Accordingly, the invention should not be deemed limited to the specific embodiments described above, but instead only by a fair scope of the claims that follow along with their equivalents.

What is claimed is:

1. An orthodontic brace for moving the relative positions of the mandibular and maxillary dental arches comprising:
    an orthodontic molar appliance adapted for connection to a tooth;
    a telescoping assembly having a first member and a second member slidably coupled to the first member for movement along a reference axis, the second member having an outer end portion; and
    a tension member connected to the outer end portion and to the molar appliance, wherein the tension member has a central axis that extends at a non-zero angle relative to the reference axis, and wherein the tension member is in tension and extends in length as the mandibular and maxillary dental arches are closed.

2. An orthodontic brace according to claim 1 wherein the tension member has a mesial end segment connected to the outer end portion of the second member and a distal end segment connected to the molar appliance, and wherein a position of the distal end segment relative to the molar appliance is incrementally adjustable.

3. An orthodontic brace according to claim 1 wherein the tension member has a mesial end segment connected to the outer end portion of the second member and a distal end segment connected to the molar appliance, and including an adjustable coupling interconnecting the distal end segment and the molar appliance.

4. An orthodontic brace according to claim 3 wherein the coupling comprises a wire section.

5. An orthodontic brace according to claim 4 wherein the wire section comprises a loop.

6. An orthodontic brace according to claim 1 and including a wire segment coupled to the molar appliance and extending along at least a portion of the mandibular arch.

7. An orthodontic brace according to claim 6 wherein the brace further includes a mandibular archwire, and wherein the wire segment extends substantially along the entire mandibular arch in parallel relationship to the mandibular archwire.

8. An orthodontic brace according to claim 6 wherein the wire segment extends in a direction generally parallel to the occlusal plane of the patient.

9. An orthodontic brace according to claim 1 and including a third member that is slidable relative to the first member.

10. An orthodontic brace according to claim 9 wherein the third member is tubular, and wherein the first member is movable in the third member.

11. An orthodontic brace according to claim 1 wherein the tension member is a coil spring.

12. An orthodontic brace for moving the relative positions of the mandibular and maxillary dental arches comprising:
    an orthodontic molar appliance adapted for connection to a molar tooth;
    a wire segment coupled to the molar appliance and adapted to extend along one of the dental arches;
    a telescoping assembly having a first member and a second member slidably coupled to the first member for movement along a reference axis, the second member having an outer end portion; and
    a coil spring connected to the outer end portion, wherein the wire segment extends through the coil spring in coaxial relationship and at a non-zero angle relative to the reference axis, wherein the coil spring is in tension when the mandibular and maxillary dental arches are closed, and wherein the coil spring expands along the wire segment and extends in length as the mandibular and maxillary dental arches are closed.

13. An orthodontic brace according to claim 12 wherein the coil spring has a mesial end segment connected to the outer end portion of the second member and a distal end segment connected to the molar appliance, and wherein a position of the distal end segment relative to the molar appliance is incrementally adjustable.

14. An orthodontic brace according to claim 12 wherein the coil spring has a mesial end segment connected to the outer end portion of the second member and a distal end segment connected to the molar appliance, and including an adjustable coupling interconnecting the distal end segment and the molar appliance.

15. An orthodontic brace according to claim 14 wherein the coupling comprises a wire section.

16. An orthodontic brace according to claim 15 wherein the wire section comprises a loop.

17. An orthodontic brace according to claim 12 wherein the wire segment extends along at least a portion of the mandibular arch.

18. An orthodontic brace according to claim 17 wherein the brace further includes a set of brackets and a mandibular archwire received in slots of the brackets, and wherein the wire segment extends substantially along the entire mandibular arch in parallel relationship to the mandibular archwire.

19. An orthodontic brace according to claim 12 wherein the wire segment extends in a direction generally parallel to the occlusal plane of the patient.

20. An orthodontic brace according to claim 12 and including a third member that is slidable relative to the first member.

21. An orthodontic brace according to claim 20 wherein the third member is tubular, and wherein the first member is movable in the third member.

\* \* \* \* \*